United States Patent
Zhou et al.

(10) Patent No.: US 12,011,612 B2
(45) Date of Patent: Jun. 18, 2024

(54) SYSTEMS AND METHODS FOR ROBUST RADIATION TREATMENT PLANNING

(71) Applicant: SHANGHAI UNITED IMAGING HEALTHCARE CO., LTD., Shanghai (CN)

(72) Inventors: Jingjie Zhou, Shanghai (CN); Supratik Bose, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 763 days.

(21) Appl. No.: 17/102,472

(22) Filed: Nov. 24, 2020

(65) Prior Publication Data

US 2021/0077827 A1    Mar. 18, 2021

Related U.S. Application Data

(63) Continuation of application No. PCT/CN2019/084548, filed on Apr. 26, 2019.

(51) Int. Cl.
*A61N 5/10* (2006.01)
*G06T 7/11* (2017.01)
(Continued)

(52) U.S. Cl.
CPC ............. *A61N 5/103* (2013.01); *G06T 7/11* (2017.01); *G06T 7/136* (2017.01); *G06T 7/149* (2017.01);
(Continued)

(58) Field of Classification Search
None
See application file for complete search history.

(56) References Cited

U.S. PATENT DOCUMENTS

| 8,222,616 | B2 * | 7/2012 | Lu | ........................... A61N 5/103 |
| | | | | 250/492.23 |
| 8,306,185 | B2 * | 11/2012 | Bal | ........................ G16H 20/40 |
| | | | | 378/65 |

(Continued)

FOREIGN PATENT DOCUMENTS

| CN | 103914823 A | 7/2014 |
| CN | 104888355 A | 9/2015 |

(Continued)

OTHER PUBLICATIONS

International Search Report in PCT/CN2019/084548 dated Jun. 27, 2019, 4 pages.

(Continued)

*Primary Examiner* — Thomas R Artman
(74) *Attorney, Agent, or Firm* — METIS IP LLC

(57) ABSTRACT

The present disclosure is related to systems and methods for generating a radiation treatment plan for a treatment volume of a subject. The method includes retrieving a planning image of the treatment volume. The planning image may include a plurality of first voxels. The method also includes retrieving a treatment image that represents at least part of the treatment volume. The treatment image may include a plurality of second voxels. For at least one of the plurality of second voxels, the method further includes determining at least one reference voxel among the plurality of first voxels in the planning image and determining a dose value corresponding to the at least one second voxel. The method still further includes generating a radiation treatment plan based at least part on the dose value corresponding to the at least one second voxel.

18 Claims, 9 Drawing Sheets

(51) Int. Cl.
*G06T 7/136* (2017.01)
*G06T 7/149* (2017.01)
*G06T 7/33* (2017.01)
*G16H 30/40* (2018.01)

(52) U.S. Cl.
CPC .............. *G06T 7/337* (2017.01); *G16H 30/40* (2018.01); *G06T 2207/20104* (2013.01); *G06T 2207/30096* (2013.01)

(56) References Cited

U.S. PATENT DOCUMENTS

| | | | |
|---|---|---|---|
| 9,694,204 B2* | 7/2017 | Hårdemark | A61N 5/1031 |
| 10,029,121 B2* | 7/2018 | Li | A61B 5/055 |
| 10,137,314 B2* | 11/2018 | Fredriksson | A61N 5/1077 |
| 10,485,990 B2* | 11/2019 | Willcut | G06T 7/11 |
| 10,722,731 B2* | 7/2020 | Maltz | A61N 5/1031 |
| 10,918,885 B2* | 2/2021 | Haas | A61B 6/466 |
| 11,318,327 B2* | 5/2022 | Willcut | G06T 7/0014 |
| 11,354,800 B2* | 6/2022 | Bose | A61N 5/1038 |
| 11,369,805 B2* | 6/2022 | Maltz | A61N 5/1038 |
| 11,623,106 B2* | 4/2023 | Haas | G06T 7/337 378/65 |
| 2009/0110145 A1* | 4/2009 | Lu | A61N 5/103 378/65 |
| 2011/0103551 A1 | 5/2011 | Bal et al. | |
| 2016/0051840 A1 | 2/2016 | Hardemark | |
| 2016/0310761 A1 | 10/2016 | Li et al. | |
| 2018/0117357 A1 | 5/2018 | Fredriksson et al. | |
| 2019/0070436 A1* | 3/2019 | Willcut | A61N 5/1039 |
| 2019/0099619 A1 | 4/2019 | Maltz | |
| 2020/0061389 A1* | 2/2020 | Willcut | A61N 5/1031 |
| 2020/0101319 A1* | 4/2020 | Haas | G06T 7/38 |
| 2020/0353287 A1* | 11/2020 | Maltz | A61N 5/1064 |
| 2021/0077827 A1* | 3/2021 | Zhou | G06T 7/149 |
| 2021/0138265 A1* | 5/2021 | Haas | A61B 6/466 |
| 2021/0201475 A1* | 7/2021 | Bose | G06T 7/337 |
| 2022/0233884 A1* | 7/2022 | Maltz | A61N 5/1064 |
| 2022/0309662 A1* | 9/2022 | Bose | G06T 7/149 |
| 2023/0211179 A1* | 7/2023 | Haas | G06T 7/337 382/128 |

FOREIGN PATENT DOCUMENTS

| | | | |
|---|---|---|---|
| CN | 105031833 A | * 11/2015 | |
| CN | 105031833 B | * 2/2018 | |
| FR | 3004654 A1 | * 10/2014 | A61N 5/1038 |
| WO | 2011053802 A2 | 5/2011 | |

OTHER PUBLICATIONS

Written Opinion in PCT/CN2019/084548 dated Jun. 27, 2019, 4 pages.

Q. Jackie Wu et al., On-Line Re-Optimization of Prostate IMRT Plans for Adaptive Radiation Therapy, Physics in Medicine and Biology, 53: 673-691, 2008.

Q. Jackie Wu et al., On-Line Re-Optimization of Prostate IMRT Plan for Adaptive Radiation Therapy—A Feasibility Study and Implementation, Danthai Thongphiew, 2008, 129 pages.

Weiguo Lu et al., Adaptive Fractionation Therapy: I. Basic Concept and Strategy, Physics in Medicine and Biology, 53: 5495-5511, 2008.

Mingli Chen et al., Adaptive Fractionation Therapy: II. Biological Effective dose, Physics in Medicine and Biology, 53: 5513-5525, 2008.

Ergun E. Ahunbay et al., An On-Line Replanning Scheme for Interfractional Variations, Medical Physics, 35(8): 3607-3615, 2008.

Yu Lei et al., A Hybrid Strategy of Offline Adaptive Planning and Online Image Guidance for Prostate Cancer Radiotherapy, Physics in Medicine and Biology, 55(8): 2221-2234, 2010.

Velibor V. Mišić et al., Adaptive and Robust Radiation Therapy Optimization for Lung Cancer, University of Toronto, 2011, 43 pages.

Ergun E. Ahunbay et al., Gradient Maintenance: A New Algorithm for Online Replanning, Medical Physics, 42(6): 2863-2876, 2015.

Rojano Kashani et al., Objective Assessment of Deformable Image Registration in Radiotherapy: A Multi-Institution Study, Medical Physics, 35(12): 5944-5953, 2008.

Noriyuki Kadoya et al., Evaluation of Various Deformable Image Registration Algorithms For Thoracic Images, Journal of Radiation Research, 55: 175-182, 2014.

Ihab S Ramadaan et al., Validation of Varian's SmartAdapt® Deformable Image Registration Algorithm for Clinical Application, Radiation Oncology, 2015, 9 pages.

Timothy C.Y. Chan et al., Adaptive and Robust Radiation Therapy Optimization for Lung Cancer, European Journal of Operational Research, 231: 745-756, 2013.

Gunilla Borgefors, Distance Transformations in Digital Images, Computer Vision, Graphics, and Image Processing, 34: 344-371, 1986.

George J. Grevera, The "Dead Reckoning" Signed Distance Transform, Computer Vision and Image Understanding, 95: 317-333, 2004.

Manu Sethi et al., The Schrödinger Distance Transform (SDT) for Point-Sets and Curves, Proceedings 2012 IEEE Conference on Computer Vision & Pattern Recognition, 2012, 8 pages.

First Office Action in Chinese Application No. 201980043079.7 dated Jul. 15, 2022, 13 pages.

* cited by examiner

500

| 501 | Retrieving a planning image of a treatment volume of a subject, the planning image including a plurality of first voxels, each of the plurality of first voxels corresponding to an initial dose value |

↓

| 502 | Retrieving a treatment image that represents at least part of the treatment volume, the treatment image including a plurality of second voxels |

↓

| 503 | Registering the treatment image with the planning image to obtain a mapping relationship between the plurality of second voxels in the treatment image and the plurality of first voxels in the planning image |

↓

| 504 | For at least one of the plurality of second voxels, determining at least one reference voxel among the plurality of first voxels in the planning image, the at least one reference voxel being located within a distance away from at least one first voxel corresponding to the at least one of the plurality of second voxels based on the mapping relationship |

↓

| 505 | Determining a dose value corresponding to the at least one second voxel based on the at least one initial dose value corresponding to the at least one reference voxel |

↓

| 506 | Generating a radiation treatment plan based at least part on the dose value corresponding to the at least one second voxel |

┌─────────────────────────────────────────────────┐
│ For each of at least one reference voxel, determining its │ 801
│ distance with respect to the defined boundary of the │
│ VOI in the planning image │
└─────────────────────────────────────────────────┘
                          ↓
┌─────────────────────────────────────────────────┐
│ For each of the at least one second voxel, determining │ 802
│ its distance with respect to the target boundary of the │
│ VOI in the treatment image │
└─────────────────────────────────────────────────┘
                          ↓
┌─────────────────────────────────────────────────┐
│ For each of the at least one reference voxel, │
│ determining a dose per unit distance value based on a │ 803
│ corresponding initial dose value and its corresponding │
│ distance with respect to the defined boundary of the │
│ VOI in the planning image │
└─────────────────────────────────────────────────┘
                          ↓
┌─────────────────────────────────────────────────┐
│ Determining a dose value corresponding to the at least │
│ one second voxel based on an average of the dose per │ 804
│ unit distance values and the distance of the at least one │
│ second voxel with respect to the target boundary of the │
│ VOI in the treatment image │
└─────────────────────────────────────────────────┘

FIG. 8

SYSTEMS AND METHODS FOR ROBUST RADIATION TREATMENT PLANNING

CROSS-REFERENCE TO RELATED APPLICATIONS

This application is a continuation of International Application No. PCT/CN2019/084548 field on Apr. 26, 2019, the contents of which are hereby incorporated by reference.

TECHNICAL FIELD

The present disclosure generally relates to systems and methods for radiation therapy, and more specifically, relates to systems and methods for generating an online robust radiation treatment re-planning in radiation therapy.

BACKGROUND

Radiation therapy (RT) has been widely employed in cancer therapy by directing radiation rays towards a tumor. Conventionally, an original radiation therapy treatment plan for a patient is generated before treatment starts. Total dose determined in the original radiation therapy treatment plan may be delivered to the patient during one or more treatment fractions, lasting for a treatment period of multiple days. However, during the treatment period, the anatomy of the tumor or other tissues (e.g., the tissue surrounding the tumor) may change. For example, the tumor may grow, deform, or shrink. Accordingly, the treatment plan may need to be updated online or offline in order to reduce toxicity and improve the overall outcome of the treatment. In some embodiments, the challenge of online re-planning is to reduce the time for the re-contouring of target regions (e.g., the tumor) and/or organs in a treatment image and to have a re-optimized plan generation based on such generated contours. All these activities need to be finished in a very short time (few minutes) to minimize the patient discomfort during this period. Thus, it is desirable to provide systems and methods for generating an online robust radiation treatment re-planning for a treatment volume of a subject in radiation therapy in a relatively short time.

SUMMARY

According to an aspect of the present disclosure, a method for generating a radiation treatment plan for a treatment volume of a subject may be implemented on at least one machine each of which may include at least one processor and at least one storage device. The method may include retrieving a planning image of the treatment volume. The planning image may include a plurality of first voxels. Each of the plurality of first voxels may correspond to an initial dose value. The method may include retrieving a treatment image that represents at least part of the treatment volume. The treatment image may include a plurality of second voxels. The method may include registering the treatment image with the planning image to obtain a mapping relationship between the plurality of second voxels in the treatment image and the plurality of first voxels in the planning image. For at least one of the plurality of second voxels, the method may include determining at least one reference voxel among the plurality of first voxels in the planning image. The at least one reference voxel may be located within a distance away from at least one first voxel corresponding to the at least one of the plurality of second voxels based on the mapping relationship. The method may include determining a dose value corresponding to the at least one second voxel based on the at least one initial dose value of the at least one reference voxel. The method may include generating a radiation treatment plan based at least part on the dose value corresponding to the at least one second voxel.

In some embodiments, each of the plurality of first voxels may correspond to a first feature value. Each of the plurality of second voxels may correspond to a second feature value. The method may include determining the at least one first voxel corresponding to the at least one of the plurality of second voxels based on the mapping relationship. The method may include determining a set of first voxels nearby the at least one first voxel corresponding to the at least one of the plurality of second voxels. The method may include designating, among the set of first voxels, at least one first voxel whose first feature value is equal to or close to the at least one second feature value of the at least one of the plurality of second voxels as the at least one reference voxel.

In some embodiments, the first feature value corresponding to a first voxel may include a gray value of the first voxel or a Hounsfield unit (HU) value corresponding to the first voxel.

In some embodiments, the treatment volume may include a volume of interest (VOI) which is represented in the planning image and in the treatment image. The VOI in the planning image may have a defined boundary. The method may include performing at least one deformable registration to obtain a deformation vector field (DVF) between the VOI in the treatment image and the VOI in the planning image. The method may include determining a target boundary of the VOI in the treatment image at least by applying the DVF on the defined boundary of the VOI in the planning image.

In some embodiments, the method may include applying the DVF on the defined boundary of the VOI in the planning image to obtain a preliminary contour of the VOI in the treatment image. The method may include modifying the preliminary contour of the VOI in the treatment image to obtain the target boundary.

In some embodiments, the method may include, for each of the at least one reference voxel, determining its distance with respect to the defined boundary of the VOI in the planning image. The method may include, for each of the at least one second voxel, determining its distance with respect to the target boundary of the VOI in the treatment image. The method may include determining the dose value corresponding to the at least one second voxel based on the at least one initial dose value of the at least one reference voxel, the at least one distance of the at least one reference voxel with respect to the defined boundary of the VOI in the planning image, and the at least one distance of the at least one second voxel with respect to the target boundary of the VOI in the treatment image.

In some embodiments, the distance of each of the at least one reference voxel with respect to the defined boundary of the VOI in the planning image may be the closest distance from each reference voxel to the defined boundary of the VOI in the planning image.

In some embodiments, for each of the plurality of first voxels, its corresponding first feature value and its distance with respect to the defined boundary of the VOI in the planning image may be stored in a first data structure. For each of the plurality of second voxels, its corresponding second feature value and its distance with respect to the target boundary of the VOI in the treatment image may be stored in a second data structure.

In some embodiments, the method may include determining, for each of the at least one reference voxel, a dose per unit distance value based on the corresponding initial dose value and its corresponding distance with respect to the defined boundary of the VOI in the planning image. The method may include determining the dose value corresponding to the at least one second voxel based on an average of the dose per unit distance values and the distance of the at least one second voxel with respect to the target boundary of the VOI in the treatment image.

In some embodiments, the dose per unit distance value for the at least one reference voxel or the dose value corresponding to the at least one second voxel may be calculated according to parallel processing.

In some embodiments, the method may include adjusting one or more parameters in an original treatment plan associated with the planning image based at least part on the dose value corresponding to the at least one second voxel.

In some embodiments, each of the plurality of second voxels may correspond to a weight. The method may include adjusting one or more parameters in an original treatment plan associated with the planning image based on the dose value corresponding to the at least one second voxel and the weight corresponding to the at least one second voxel.

In some embodiments, the treatment volume may include a target to be treated. The plurality of second voxels in the treatment image may be associated with the treatment volume excluding the target.

According to another aspect of the present disclosure, a system may include at least one storage device storing a set of instructions, and at least one processor in communication with the at least one storage medium. Wen executing the set of instructions, the at least one processor may be configured to cause the system to retrieve a planning image of the treatment volume. The planning image may include a plurality of first voxels. Each of the plurality of first voxels may correspond to an initial dose value. The at least one processor may be configured to cause the system to retrieve a treatment image that represents at least part of the treatment volume. The treatment image may include a plurality of second voxels. The at least one processor may be configured to cause the system to register the treatment image with the planning image to obtain a mapping relationship between the plurality of second voxels in the treatment image and the plurality of first voxels in the planning image. For at least one of the plurality of second voxels, the at least one processor may be configured to cause the system to determine at least one reference voxel among the plurality of first voxels in the planning image. The at least one reference voxel may be located within a distance away from at least one first voxel corresponding to the at least one of the plurality of second voxels based on the mapping relationship. The at least one processor may be configured to cause the system to determine a dose value corresponding to the at least one second voxel based on the at least one initial dose value of the at least one reference voxel. The at least one processor may be configured to cause the system to generate a radiation treatment plan based at least part on the dose value corresponding to the at least one second voxel.

According to another aspect of the present disclosure, a non-transitory computer readable medium may include at least one set of instructions. When executed by at least one processor of a computing device, the at least one set of instructions may cause the at least one processor to effectuate a method. The method may include retrieving a planning image of the treatment volume. The planning image may include a plurality of first voxels. Each of the plurality of first voxels may correspond to an initial dose value. The method may include retrieving a treatment image that represents at least part of the treatment volume. The treatment image may include a plurality of second voxels. The method may include registering the treatment image with the planning image to obtain a mapping relationship between the plurality of second voxels in the treatment image and the plurality of first voxels in the planning image. For at least one of the plurality of second voxels, the method may include determining at least one reference voxel among the plurality of first voxels in the planning image. The at least one reference voxel may be located within a distance away from at least one first voxel corresponding to the at least one of the plurality of second voxels based on the mapping relationship. The method may include determining a dose value corresponding to the at least one second voxel based on the at least one initial dose value of the at least one reference voxel. The method may include generating a radiation treatment plan based at least part on the dose value corresponding to the at least one second voxel.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 5 illustrates a flowchart illustrating an exemplary process for generating a radiation treatment plan according to some embodiments of the present disclosure;

FIG. 8 illustrates a flowchart illustrating an exemplary process for determining a dose value corresponding to a second voxel according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
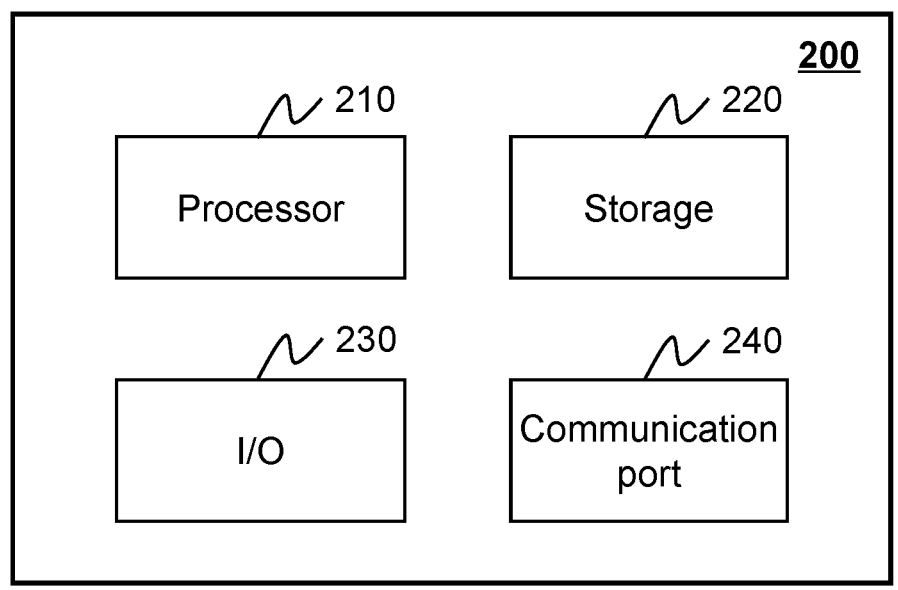
FIG. 2 is a schematic diagram illustrating exemplary hardware and/or software components of an exemplary computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

An aspect of the present disclosure relates to systems and methods for generating a robust radiation treatment re-planning for a treatment volume of a subject. For example, before a certain treatment fraction, the systems and methods may obtain an "on-spot" treatment image (also referred to as "treatment image" for short) of the treatment volume. The systems and methods may also retrieve the original treatment plan associated with the planning image (i.e., the image used to generate the original treatment plan) of the treatment volume. The systems and methods may further register the treatment image with the planning image to obtain a mapping relationship between them. For at least one voxel in the treatment image, the systems and methods may determine one or more corresponding voxels in the planning image based on the mapping relationship. Then, the systems and methods may determine the dose value corresponding to a voxel in the treatment image based on the dose values of the corresponding voxels in the planning image. The systems and methods may further generate a robust radiation treatment re-planning based at least part on the dose values corresponding to the voxels in the treatment image. Compared to the conventional techniques, the systems and methods may generate the radiation treatment re-planning that would satisfy dose goal/restriction of both target regions (e.g., a tumor) and organs at risk (OARs) of the subject without contouring the OARs in the treatment image, thus greatly reducing the time cost in the online re-planning process.

Figure 1:
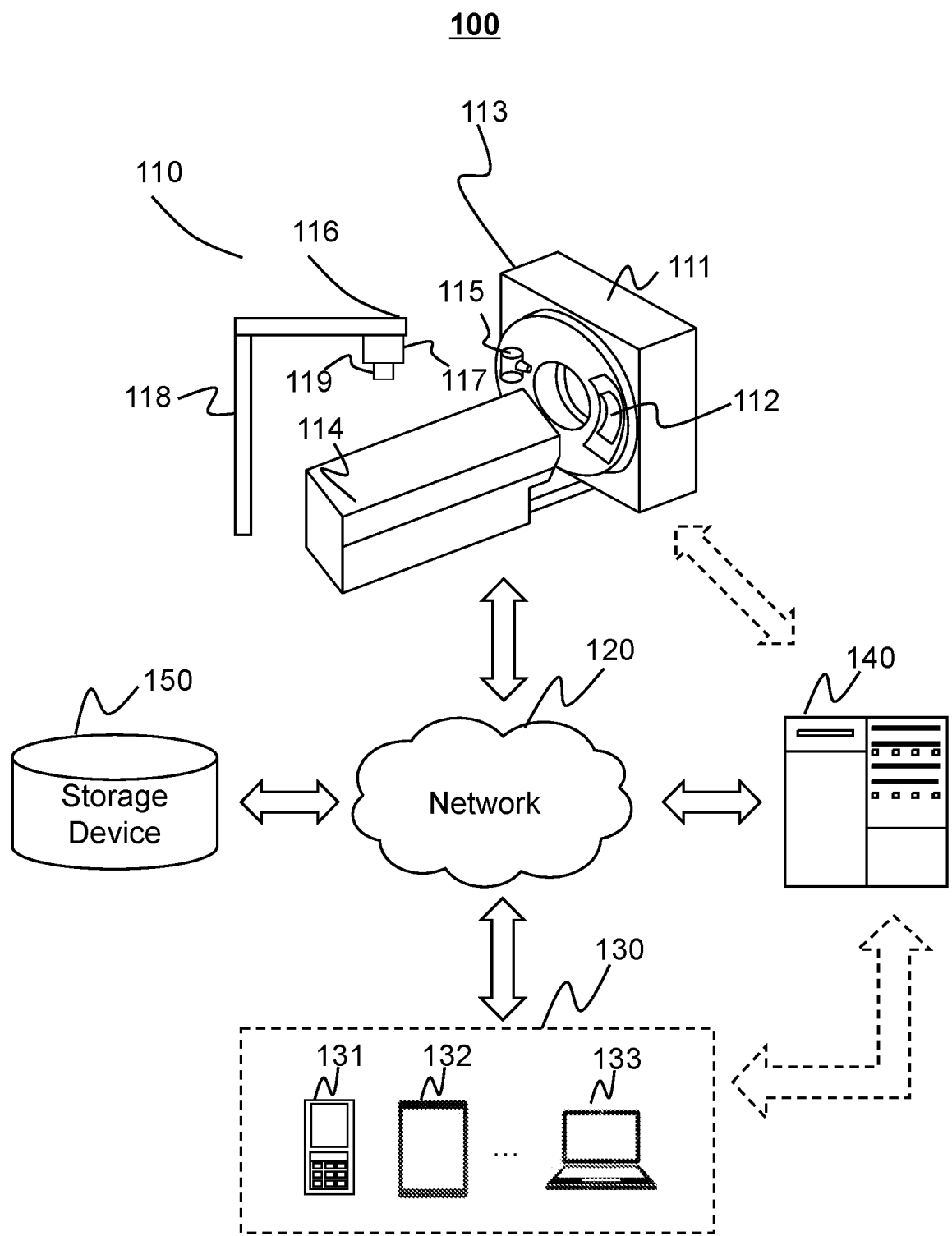
FIG. 1 is a schematic diagram illustrating an exemplary radiation system according to some embodiments of the present disclosure.

FIG. 1 is a schematic diagram illustrating an exemplary radiation therapy system 100 according to some embodiments of the present disclosure. The radiation therapy system 100 may include an imaging-treatment device 110, a network 120, one or more terminals 130, a processing device 140, and a storage device 150. The components in the radiation therapy system 100 may be connected in various ways. Merely by way of example, the imaging-treatment device 110 may be connected to the processing device 140 through the network 120. As another example, the imaging-treatment device 110 may be connected to the processing device 140 directly as indicated by the bi-directional arrow in dotted lines linking the imaging-treatment device 110 and the processing device 140. As still another example, the storage device 150 may be connected to the processing device 140 directly or through the network 120. As still another example, the terminal 130 may be connected to the processing device 140 directly (as indicated by the bi-directional arrow in dotted lines linking the terminal 130 and the processing device 140) or through the network 120.

The imaging-treatment device 110 may include an imaging component 113, a treatment component 116, a table 114, or the like.

The imaging component 113 may include a device or apparatus that is capable of providing image data of an object (e.g., a patient), such as, a computed tomography (CT) device, a magnetic resonance imaging (MRI) device, a single photon emission computed tomography (SPECT) device, a positron emission tomography (PET) device, a PET-CT device, or the like, or any combination thereof. For illustration purpose, the imaging component 113 is described as a CT device herein, and the description thereof is not intended to limit the scope of the present disclosure. As shown in FIG. 1, the imaging component 113 may include an imaging radiation source 115, a detector 112, a gantry 111, or the like. The imaging radiation source 115 and the detector 112 may be mounted on the gantry 111. The imaging radiation source 115 may emit radiation rays (e.g., X-ray) to the object (e.g., a patient) placed on the table 114. The detector 112 may detect at least a portion of the radiation rays traversing the object. In some embodiments, the detector 112 may include one or more detector units. The one or more detector units may include a scintillation detector (e.g., a cesium iodide detector, a gadolinium oxysulfide detector). The detector 112 may include a single-row detector and/or a multi-rows detector.

The imaging component 113 may generate an image of the object before, during, and/or after a radiation therapy treatment. The image of the object may be used to determine and/or track the location of a target region of the object. In some embodiments, the target region may refer to the region that needs to be radiated. In some embodiments, the target region may be a portion of the object, for example, a head, a breast, a lung, an abdomen, a large intestine, a small intestine, a bladder, a gallbladder, a pancreas, a prostate, a uterus, an ovary, a liver, or the like, or a portion thereof, or any combination thereof. In the present disclosure, "object" and "subject" are used interchangeably. In some embodiments, the target region may include an abnormal tissue, for example, a tumor, a polyp, or the like. The radiation rays may be delivered toward the target region for radiation therapy based on the determined or tracked location of the target region.

The treatment component 116 may include a device or apparatus that is capable of providing treatment beams (e.g., radiation rays). As shown in FIG. 1, the treatment component 116 may include a treatment radiation source 117, a gantry 118, and a collimator 119. In some embodiments, the treatment radiation source 117 may be a linear accelerator (LINAC) that accelerates electrons and generates radiation rays thereby. The collimator 119 may control the shape of the radiation rays to generate the treatment beams. In some embodiments, the imaging component 113 may be spaced by a distance from the treatment component 116. In some embodiments, the gantry 111 of the imaging component 113 and the gantry 118 of the treatment component 116 may share a same axis of rotation. The object may be positioned in different positions on the table 114 for imaging and treatment. In some embodiments, the imaging component 113 and the treatment component 116 may share a same gantry. For example, the gantry 118 may be omitted and the treatment radiation source 117 may be mounted on the gantry 111. An object may be placed on the table 114 for treatment and/or scan. In some embodiments, the imaging radiation source 115 and the treatment radiation source 117 may be integrated as one radiation source to image and/or treat the object. In some embodiments, the treatment radiation source 117 may be used as the imaging radiation source 115 to image and/or treat the object.

The treatment component 116 may deliver the treatment beams toward a target region of an object (e.g., a patient). The treatment beams may include a particle beam, a photon beam, or the like, or any combination thereof. The particle beam may include a stream of neutrons, protons, electrons, heavy ions, α-ray beams, or the like, or any combination thereof. The photon beams may include an X-ray beam, a γ-ray beam, an ultraviolet beam, an ultrasound beam (e.g., a high intensity focused ultrasound beam), a laser beam, or the like, or any combination thereof. The shape of the X-ray beam may be a line, a narrow pencil, a narrow fan, a fan, a cone, a wedge, or the like, or any combination thereof. The energy level of the treatment beams may be suitable for the radiation therapy. For example, an X-ray beam delivered by the treatment component 116 may have an energy of megavoltage (MV) level.

The network 120 may include any suitable network that can facilitate the exchange of information and/or data for the radiation therapy system 100. In some embodiments, one or more components of the radiation therapy system 100 (e.g., the imaging-treatment device 110, the terminal 130, the processing device 140, the storage device 150) may communicate information and/or data with one or more other components of the radiation therapy system 100 via the network 120. For example, the processing device 140 may obtain image data (e.g., a planning image, a treatment image) from the imaging-treatment device 110 via the network 120. As another example, the processing device 140 may obtain user instructions from the terminal 130 via the network 120. The network 120 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the radiation therapy system 100 may be connected to the network 120 to exchange data and/or information.

Figure 3:
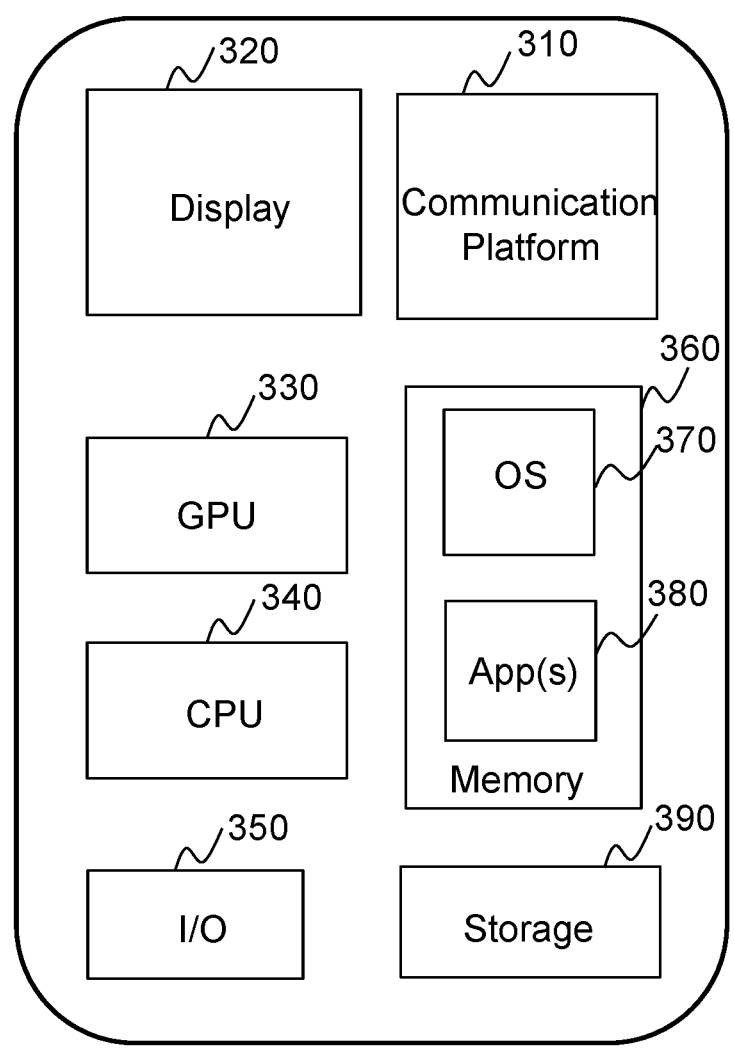
FIG. 3 is a schematic diagram illustrating exemplary hardware and/or software components of an exemplary mobile device on which the terminal may be implemented according to some embodiments of the present disclosure.

The terminal(s) 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. Merely by way of example, the terminal 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data and/or information obtained from the imaging-treatment device 110, the terminal 130, and/or the storage device 150. For example, the processing device 140 may register a treatment image with one or more planning images to obtain a mapping relationship between voxels in the treatment image and voxels in the one or more planning image. As another example, for each voxel in the treatment image, the processing device 140 may determine one or more reference voxels among the voxels in the one or more planning images. As still another example, the processing device 140 may determine a dose value corresponding to a voxel in the treatment image based on the dose values corresponding to one or more reference voxels in the one or more planning images. As still another example, the processing device 140 may generate a radiation treatment plan based at least part on the dose values corresponding to one or more voxels in the treatment image. In some embodiments, the processing device 140 may be a single server or a server group. The server group may be centralized or distributed. In some embodiments, the processing device 140 may be local to or remote from one or more other components of the radiation therapy system 100. For example, the processing device 140 may access information and/or data stored in the imaging-treatment device 110, the terminal 130, and/or the storage device 150 via the network 120. As another example, the processing device 140 may be directly connected to the imaging-treatment device 110, the terminal 130 and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the terminal(s) 130 and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the radiation therapy system 100 (e.g., the processing device 140, the terminal 130). One or more components of the radiation therapy system 100 may access the data or instructions stored in the storage device 150 via the network 120. In some embodiments, the storage device 150 may be directly connected to or communicate with one or more other components of the radiation therapy system 100 (e.g., the processing device 140, the terminal 130). In some embodiments, the storage device 150 may be part of the processing device 140.

FIG. 2 is a schematic diagram illustrating an exemplary computing device 200 on which at least a portion of the radiation therapy system 100 can be implemented, according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 210 may process image data obtained from the imaging-treatment device 110, the storage device 150, the terminal(s) 130, and/or any other component of the radiation therapy system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging-treatment device 110, the storage device 150, the terminal(s) 130, and/or any other components of the radiation therapy system 100. In some embodiments, the storage 220 may include a mass storage, removable storage, a volatile read-and-write memory, a read-only memory (ROM), or the like, or a combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for determining a dose value corresponding to a voxel in a treatment image provided by the imaging-treatment device 110.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the imaging-treatment device 110, the storage 150, and/or the terminal(s) 130. The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 on which the terminal(s) 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information may be achieved via the I/O 350 and provided to the processing device 140 and/or other components of the radiation therapy system 100 via the network 120.

To implement various modules, units, and their functionalities described in the present disclosure, computer hardware platforms may be used as the hardware platform(s) for one or more of the elements described herein. A computer with user interface elements may be used as a personal computer (PC) or any other type of work station or terminal device. A computer may also act as a server if appropriately programmed.

Figure 4:
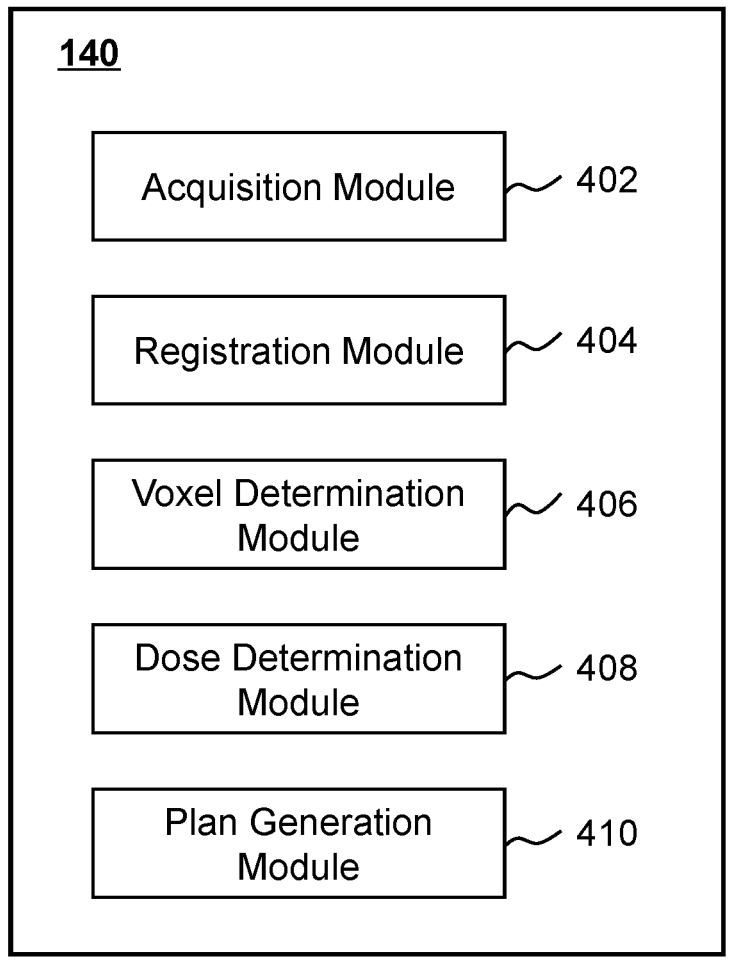
FIG. 4 is a block diagram illustrating an exemplary processing device according to some embodiments of the present disclosure.

FIG. 4 is a block diagram illustrating an exemplary processing device 140 according to some embodiments of the present disclosure. The processing device 140 may include an acquisition module 402, a registration module 404, a voxel determination module 406, a dose determination module 408, and a plan generation module 410.

The acquisition module 402 may acquire various data or information from other components of the radiation therapy system 100. For example, the acquisition module 402 may retrieve a planning image of a treatment volume of a subject. As another example, the acquisition module 402 may retrieve a treatment image that represents at least part of a treatment volume of a subject.

The registration module 404 may register a treatment image with a planning image. In some embodiments, before registering a treatment image with a planning image, the registration module 404 may preprocess the treatment image (e.g., reformat the treatment image) so that the preprocessed treatment image has the similar pixel dimension as that of the planning image. In some embodiments, after registering a treatment image with a planning image, the registration module 404 may determine a target boundary of a volume of interest (VOI) in the treatment image based on a defined boundary of the VOI in the planning image. For example, the registration module 404 may perform at least one deformable registration to obtain a deformation vector field (DVF) between the treatment image and the planning image. The registration module 404 may further apply the DVF on the defined boundary of the VOI in the planning image to obtain a preliminary contour of the VOI in the treatment image. The registration module 404 may further modify the preliminary contour of the VOI in the treatment image, according to a user instruction or by itself, to obtain the target boundary. As used herein, a VOI may refer to a volume of cancerous target which needs to be treated by the radiation therapy system 100 and/or a volume of non-cancerous object under the risk of radiation. Specifically, the VOI may be a target region (e.g., a tumor, an organ with tumor, or a tissue with tumor) and/or an OAR.

The voxel determination module 406 may determine a voxel in a planning image and/or a treatment image. In some embodiments, for at least one of a plurality of second voxels in the treatment image, the voxel determination module 406 may determine at least one reference voxels among a plurality of first voxels in the planning image. For example, the voxel determination module 406 may determine at least one first voxel corresponding to at least one of a plurality of second voxels based on a mapping relationship (e.g., a DVF determined by the registration module 404). The voxel determination module 406 may determine a set of first voxels nearby the at least one corresponding first voxel, and designate, among the set of first voxels, at least one first voxel whose first feature value is equal to or close to the second feature value of the at least one of the plurality of second voxels as the at least one reference voxel.

The dose determination module 408 may determine a dose value corresponding to a voxel. In some embodiments, the voxel determination module 406 may determine a dose value corresponding to a second voxel in a treatment image. For example, for at least one reference voxel of the second voxel, the dose determination module 408 may determine its distance with respect to a defined boundary of a VOI in a planning image. The dose determination module 408 may also determine the distance of the second voxel with respect to a target boundary of the VOI in the treatment image. The dose determination module 408 may further determine the dose value corresponding to the second voxel based on the distance of the second voxel with respect to the target boundary of the VOI in the treatment image, the distance of the at least one reference voxel with respect to the defined boundary of the VOI in the planning image, and the initial dose value corresponding to the at least one reference voxel in the planning image.

The plan generation module 410 may generate a radiation treatment plan. In some embodiments, the plan generation module 410 may determine the radiation treatment plan by adjusting one or more parameters in an original treatment plan associated with a planning image, based on the dose values corresponding to a plurality of second voxels in a treatment image. In some embodiments, the processing device 140 may adjust and/or optimize the one or more parameters according to an optimization technique as described elsewhere in the present disclosure.

It should be noted that the above description of the processing device 140 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module facilitating data storage.

FIG. 5 illustrates a flowchart illustrating an exemplary process 500 for generating a radiation treatment plan (e.g., an online radiation treatment re-planning) according to some embodiments of the present disclosure. In some embodiments, at least part of process 500 may be performed by the processing device 140 (implemented in, for example, the computing device 200 shown in FIG. 2). For example, the process 500 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 501, the processing device 140 (e.g., the acquisition module 402) may retrieve a planning image of a treatment volume of a subject. In some embodiments, the processing device 140 may retrieve the planning image of the treatment volume from a storage device (e.g., the storage device 150) of the radiation therapy system 100, or an external storage device. In some embodiments, the processing device 140 may directly retrieve the planning image from the imaging-treatment device 110.

The planning image may refer to an image that was used to determine an existing treatment plan. The planning image may include information related to a treatment volume of a subject. For example, the planning image may show the tumor as well as one or more tissues, organs nearby the tumor in the treatment volume. As used herein, an existing treatment plan may describe how a radiation therapy is performed on a subject (e.g., a patient), or more specifically, how one or more radiation beams are delivered to a treatment volume of the subject. For example, the existing treatment plan may provide the instructions of a total dosage and/or a dose distribution in the treatment volume of the subject. The dose distribution may indicate the dose values corresponding to different voxels of the treatment volume. Additionally, the existing treatment plan may include recognizing one or more organs at risk (OARs) in the treatment volume and restricting or avoiding dose thereon. The OAR may refer to an organ that is located in the vicinity of a tumor and under the risk of radiation damage due to the exposure to radiation delivered toward the tumor.

In some embodiments, the existing treatment plan may be an original treatment plan determined before or at the beginning of the course of a radiation therapy. For example, before the subject (e.g., a patient) begins to receive a treatment (e.g., days or weeks before the treatment starts), one or more planning images may be taken to generate the original treatment plan to be followed in the subsequent treatment. Alternatively, in some embodiments, for a certain fraction of a fractionated radiation therapy, the existing treatment plan may be the treatment plan used in any previous fraction (e.g., one fraction prior to the certain fraction, two fractions prior to the certain fraction). Alternatively, in some embodiments, the existing treatment plan may be a historical treatment plan of the subject.

In some embodiments, the planning image may be a cone beam CT image, an MR image, a PET-CT image, an MR-CT image, or the like. For example, the planning image may be a CT image obtained by the imaging component 113 of the imaging-treatment device 110. As another example, the planning image may be a CT image obtained by an imaging assembly outside the imaging-treatment device 110. The planning image may be a two-dimensional (2D) image, a three-dimensional (3D) image, a four-dimensional (4D) image, or the like. In some embodiments, the planning image may be obtained according to one or more instructions or manipulations of an operator (e.g., a doctor). For example, the planning image may be obtained based on one or more imaging parameters input or selected by the operator.

The subject may include a substance, a tissue, an organ, a specimen, a body, or the like, or any combination thereof. In some embodiments, the subject may include a patient or a part thereof (e.g., a head, a breast, an abdomen). In some embodiments, the treatment volume of the subject may include one or more volumes of interest (VOIs).

The planning image may include a plurality of first voxels. Each of the plurality of first voxels may correspond to a dose value indicated in the existing treatment plan (also referred to as "initial dose value"). In some embodiments, the processing device 140 may determine the initial dose values corresponding to the first voxels based on the planning image according to one or more dose calculation algorithms. Exemplary dose calculation algorithm may include a model-based algorithm (e.g., a convolution based algorithm, a superposition based algorithm, Monte Carlo dose algorithm), a correction-based algorithm, or the like, or any combination thereof.

Each of the plurality of first voxels may correspond to a first feature value. The first feature value corresponding to the first voxel may be related to the material and/or a density value of the subject corresponding to the first voxel. In some embodiments, in X-ray imaging, the first feature value corresponding to the first voxel may reflect the ability of the subject corresponding to the first voxel that attenuates the X-ray. For example, the first feature value corresponding to a first voxel may include a gray value of the first voxel or a Hounsfield unit (HU) value corresponding to the first voxel. As used herein, Hounsfield unit (HU) may refer to a dimensionless unit used in computed tomography (CT) scanning to express CT numbers in a standardized and convenient form. The CT Hounsfield scale may be calibrated such that the HU value for water is 0 HU and that for air is −1000 HU. The HU value of a voxel may indicate the type of tissue to which the voxel belongs. Voxels with similar HU values may belong to similar tissue types. In some embodiments, the HU value of a voxel may be represented as a gray value of the voxel on a visual interface (e.g., the screen of the user terminal). A higher HU value of a voxel may correspond to a higher gray value in a CT image.

In some embodiments, the processing device 140 may identify the position of each of the plurality of first voxels. For example, according to the planning image, the processing device 140 may identify a boundary of the VOI (e.g., a tumor) in the treatment volume and determine the distance of each first voxel with respect to the boundary. Exemplary distance may include a Euclidean distance, a taxicab distance, a Chamfers distance, a dead-reckoning distance, a Schrodinger distance, or the like. In some embodiments, the distance of a first voxel with respect to the boundary of the VOI in the treatment volume may be the closest distance from the first voxel to the boundary of the VOI in the treatment volume. Specifically, the processing device 140 may determine the closest distance from a first voxel to the boundary of the VOI in the treatment volume based on a signed distance function (SDF). As used herein, the SDF may represent the closest distance from a given point A (e.g., a voxel) to a boundary of an area B (e.g., a VOI), with the sign determined by whether point A is in area B or on the boundary of area B. The SDF may be positive, zero, or negative in response to that point A is outside, on the boundary of, or inside area B, respectively. The processing device 140 may determine the SDF for each first voxel based on one or more SDF algorithms. Exemplary SDF algorithm may include a fast marching technique, a fast sweeping technique, a level set technique, or the like, or any combination thereof.

In some embodiments, the initial dose values of the first voxels indicated in the existing treatment plan (also referred to as "the planned dose values") may be different from the ideal dose values of the first voxels. As used herein, the ideal dose value of a voxel corresponding to a target (e.g., a tumor) may be a prescribed dose value while the ideal dose value of a voxel corresponding to an OAR may be zero. In some embodiments, each of the plurality of first voxels may be assigned with a weight, and the difference between the planned dose values and the ideal dose values may be measured by a weighted sum of the difference between each planned dose value and the corresponding ideal dose value. The weight of the first voxel may be determined by one or more components of the radiation therapy system 100 (e.g., the processing device 140) or may be set by an operator. In some embodiments, the weight of the first voxel may be determined according to its distance with respect to the boundary of the VOI in the treatment volume. For example, a greater weight may be assigned to a first voxel that is closer to the boundary of the VOI in the treatment volume (along a specific direction). In some embodiments, the weight of the first voxel may be determined according to a radiosensitivity of the subject corresponding to the first voxel. The radiosensitivity of the subject may refer to a relative susceptibility of the subject to the harmful effect of radiation. For example, a greater weight may be assigned to a first voxel if the subject corresponding to the first voxel is more sensitive to the radiation. In this regard, in calculating the weighed sum of the difference between each planned dose value and the corresponding ideal dose value, more weight may be given to the difference between the planned dose value and the ideal dose value when the corresponding OAR is more sensitive or closer to the target (e.g., a tumor).

In some embodiments, the processing device 140 may store the information related to each first voxel in a storage device (e.g., the storage device 150) of the radiation therapy system 100, or an external storage device. The information related to a first voxel may include its distance with respect to the defined boundary of the VOI (i.e., a tumor) in the treatment volume, the initial dose value corresponding to the first voxel, the first feature value corresponding to the first voxel, and/or the weight corresponding to the first voxel. The information related to the first voxel may be recorded in the form of a table, a map, a mathematical expression (e.g., a hash function), or the like. Further, in some embodiments, the processing device 140 may store the relationship between a first voxel and its nearby voxels such that when the first voxel is accessed, its nearby voxels as well as their information can be easily identified. As used herein, "a nearby voxel of a first voxel" may refer to that a distance between the first voxel and the nearby voxel is less than a preset distance threshold.

In 502, the processing device 140 (e.g., the acquisition module 402) may retrieve a treatment image that represents at least part of the treatment volume. In some embodiments, the processing device 140 may retrieve the treatment image from the imaging component 113, a storage device (e.g., the storage device 150) of the radiation therapy system 100, or an external storage device.

The treatment image may refer to an image that is used to adjust the original treatment plan associated with the planning image. In some embodiments, the treatment image may be generated a relatively short time before a certain treatment fraction starts. The relatively short time may be several days, several hours, or several minutes, depending on the duration of all the courses of the radiation therapy. The treatment image, compared with the planning image, may reflect a change of the treatment volume (or the VOI(s) in the treatment volume) during, for example, the previous treatment fraction and this certain treatment fraction. The change of the treatment volume (or the VOI(s) in the treatment volume) may include an anatomical change (e.g., weight loss, shrinkage of tumor, appearance of new tumor), etc. The original treatment plan may be adjusted and/or modified based on the treatment image in order to reduce toxicity to the OAR(s) and improve targeting of the target (e.g., the tumor) and overall outcome of the treatment.

In some embodiments, the treatment image may be a CT image, a cone beam CT image, an MR image, a PET-CT image, or the like. For example, the treatment image may be a CT image obtained by the imaging component 113 of the imaging-treatment device 110. The treatment image may be a two-dimensional (2D) image, a three-dimensional (3D) image, a four-dimensional (4D) image, or the like. In some embodiments, the treatment image may be obtained according to one or more instructions or manipulations of an operator (e.g., a doctor). For example, the treatment image may be obtained based on one or more imaging parameters input or selected by the operator. In some embodiments, the treatment image and the planning image may be the same type of image. For example, both the treatment image and the planning image may be CT images, and the treatment image may be directly generated by a CT device. Alternatively, the treatment image may be converted from another type of image (e.g., an MR image) that is generated by a device other than a CT device.

The treatment image may include a plurality of second voxels. In some embodiments, each of the plurality of second voxels may correspond to a second feature value. The second feature value corresponding to a second voxel may include a gray value of the second voxel or a Hounsfield unit (HU) value corresponding to the second voxel.

In 503, the processing device 140 (e.g., the registration module 404) may register the treatment image with the planning image to obtain a mapping relationship between the plurality of second voxels in the treatment image and the plurality of first voxels in the planning image.

As used herein, image registration is a process of transforming the spatial information of different images into a same coordinate system in order to compare or integrate the data obtained from the different images. The processing device 140 may register the treatment image with the planning image based on one or more image registration algorithms. Exemplary image registration algorithm may include an intensity-based algorithms, a feature-based algorithm, a transformation model algorithm (e.g., a linear transformation model, a non-rigid transformation model), a spatial domain algorithm, a frequency domain algorithm, a single-modality algorithm, a multi-modality algorithm, an automatic algorithms, and an interactive algorithms, or the like, or a combination thereof.

In some embodiments, before registering the treatment image with the planning image, the processing device 140 may reformat the treatment image so that it has the similar pixel dimension as that of the planning image. For example, the pixel dimension of the planning image may be 512×512 pixels, and the pixel dimension of the treatment image may be 1024×1024 pixels. The processing device 140 may reformat the treatment image to transfer the pixel dimension of the treatment image from 1024×1024 pixels to 512×512 pixels.

In some embodiments, the processing device 140 may register the treatment image and the planning image by performing one or more rigid registrations and/or one or more deformable registrations (also referred to as non-rigid registration).

The rigid registration may refer to a registration procedure that involves global rotation(s) and/or translation(s) of all voxels. The rigid registration between the treatment image and the planning image may align the treatment image to the planning image so that the internal anatomy (e.g., the anatomy of the target or OAR) within the treatment image is at the same or substantially the same position with respect to the external radiation beams as that of the planning image. In some embodiments, a setup error (e.g., a couch translation and/or a couch rotation) may be corrected based on the rigid registration process. After correcting the setup error on the treatment image, the internal anatomy of the subject at treatment time with respect to the external radiotherapy beams may be at the same position as was planned between the planning image and the external radiotherapy beams.

The deformable registration may refer to a process of finding a point to point (e.g., voxel to voxel) mapping relationship between the planning image and the treatment image. In some embodiments, the processing device 140 may determine a deformation vector field (DVF) that represents the mapping relationship between the plurality of second voxels in the treatment image and the plurality of first voxels in the planning image. Accordingly, provided that the VOI in the planning image has a defined boundary, the processing device 140 may identify the boundary the VOI in the treatment image based on the DVF. For example, the processing device 140 may apply the DVF on the defined boundary of the VOI in the planning image to obtain a preliminary contour of the VOI in the treatment image. In some embodiments, the processing device 140 may modify the preliminary contour of the VOI in the treatment image according to, for example, a first user instruction to obtain a target boundary of the VOI in the treatment image. The first user instruction may indicate an adjustment of at least a portion of the preliminary contour of the VOI in the treatment image. In some embodiments, the processing device 140 may designate the preliminary contour of the VOI in the treatment image as the target boundary of the VOI in the treatment directly, or in response to a second user instruction including a confirmation message. More descriptions of the determination of the target boundary of the VOI in the treatment image may be found elsewhere in the present disclosure (e.g., FIG. 6 and the descriptions thereof).

In some embodiments, the processing device 140 may firstly perform the rigid registration, and then perform the deformable registration to generate the DVF. In some embodiments, the processing device 140 may directly perform the deformable registration, without performing any previous rigid registration, to generate the DVF.

In some embodiments, the mapping relationship between the plurality of second voxels in the treatment image and the plurality of first voxels in the planning image may be stored in the form of a table, a map, a mathematical expression, or the like. Thus, when a first voxel in the planning image is retrieved, its corresponding second voxel in the treatment image may be easily identified. Similarly, when a second voxel in the treatment image is retrieved, its corresponding first voxel in the planning image may be easily identified.

In 504, for at least one of the plurality of second voxels, the processing device 140 (e.g., the voxel determination module 406) may determine at least one reference voxel among the plurality of first voxels in the planning image. The at least one reference voxel may be located within a distance away from the at least one first voxel corresponding to the at least one of the plurality of second voxels based on the mapping relationship.

In some embodiments, for a specific second voxel (of the at least one of the plurality of second voxels) in the treatment image, the processing device 140 may determine a corresponding first voxel in the planning image based on the mapping relationship between the plurality of second voxels in the treatment image and the plurality of first voxels in the planning image. For example, the processing device 140 may apply an inversion of the DVF on the specific second voxel in the treatment image to obtain the corresponding first voxel in the planning image. As another example, the processing device 140 may retrieve a table illustrating the one-to-one correspondence between the plurality of first voxels in the planning image and the plurality of second voxels in the treatment image, thereby identifying the corresponding first voxel of the specific second voxel.

The processing device 140 may further determine a set of first voxels nearby the corresponding first voxel. In some embodiments, the processing device 140 may determine the set of first voxels based on the distance between each of the plurality of first voxels and the corresponding first voxel in the planning image. For example, the processing device 140 may determine whether the distance between each of the plurality of first voxels and the corresponding first voxel is smaller than the distance threshold. In response to a determination that the distance between a certain first voxel and the corresponding first voxel is smaller than the distance threshold. The processing device 140 may determine that the first voxel is in the set of first voxels.

Further, the processing device 140 may select the at least one reference voxel from the set of first voxels. For example, the processing device 140 may designate, among the set of first voxels nearby the corresponding first voxel, one or more first voxels whose first feature values satisfy a specific rule as one or more reference voxels. The specific rule may be that the first feature value of the first voxel is equal to or close to the second feature value of the specific second voxel. More descriptions of the determination of one or more reference voxels corresponding to a second voxel may be found elsewhere in the present disclosure (e.g., FIG. 7 and the descriptions thereof).

In 505, the processing device 140 (e.g., the dose determination module 408) may determine a dose value corresponding to the at least one second voxel based on the at least one initial dose value corresponding to the at least one reference voxel.

In some embodiments, the processing device 140 may determine the dose value corresponding to the at least one second voxel by performing a mathematic operation to the at least one initial dose value corresponding to the at least one reference voxel. For example, the processing device 140 may calculate an average value of the initial dose value corresponding to the at least one reference voxel, and then calculate the dose value corresponding to the at least one second voxel based on the average value. As another example, the processing device 140 may calculate a weighted average value of the initial dose value corresponding to the at least one reference voxel, and then calculate the dose value corresponding to the at least one second voxel based on the weighted average value. The weighting factor associated with each initial dose value may be related to the position of the corresponding reference voxel, e.g., the distance of the corresponding reference voxel with respect to the defined boundary of the VOI in the planning image.

An exemplary weighted average is described herein for illustration purpose, and is not intended for limiting. For each of the at least one reference voxel corresponding to the at least one second voxel, the processing device 140 may determine a dose per unit distance value (i.e., the weighted dose value) based on its initial dose and its distance with respect to the defined boundary of the VOI in the planning image. The dose per unit distance value of the reference voxel may be generated by dividing its initial dose by its distance with respect to the defined boundary of the VOI in the planning image. The processing device 140 may further determine an average of the dose per unit distance values of the at least one reference voxel to generate the weighted average value of the at least one reference voxel. The average of the dose per unit distance values may be an arithmetic mean, a harmonic mean, a geometric mean, or the like. More descriptions of the weighted average may be found elsewhere in the present disclosure (e.g., FIG. 8 and the descriptions thereof).

The processing device 140 may further determine the dose value corresponding to a second voxel based on the weighted average value of the at least one reference voxel and the distance of the second voxel with respect to the target boundary of the VOI in the treatment image. For example, the processing device 140 may determine the dose value corresponding to the second voxel by multiplying the weighted average value of the at least one reference voxel and the distance of the second voxel with respect to the target boundary of the VOI in the treatment image. More descriptions of the determination of a dose value corresponding to a second voxel may be found elsewhere in the present disclosure (e.g., FIG. 8 and the descriptions thereof).

In some embodiments, similar to the plurality of first voxels described in connection with 501, each of the plurality of second voxels may also correspond to a weight. In some embodiments, the weight of the second voxel may be determined based on the weight of its corresponding first voxel in the planning image. For example, the weight of the second voxel may be the same as the weight of its corresponding first voxel in the planning image. In some embodiments, the weight of the second voxel may be determined according to its distance with respect to the boundary of the VOI in the treatment volume. For example, a greater weight may be assigned to a second voxel that is closer to the boundary of the VOI in the treatment volume (along a specific direction). In some embodiments, the weight of the second voxel may be determined according to a radiosensitivity of the subject corresponding to the second voxel. For example, a greater weight may be assigned to a second voxel if the subject corresponding to the second voxel is more sensitive to the radiation.

In 506, the processing device 140 (e.g., the plan generation module 410) may generate a radiation treatment plan based at least part on the dose value corresponding to the at least one second voxel.

In some embodiments, the processing device 140 may determine the radiation treatment plan by updating/adjusting one or more parameters in the original treatment plan associated with the planning image. The one or more parameters may describe how a radiation therapy is performed on a subject (e.g., a patient). In some embodiments, the one or more parameters may include a machine radiation parameter and a geometrical parameter. The machine radiation parameter may include a radiation dose, a dose rate (e.g., MUs/min) provided by a radiation source, the duration of radiation, a modality type information (e.g., photons, electrons) provided by the radiation source, or the like, or any combination thereof. The geometrical parameter may include a position of the gantry, an angle of the gantry at a certain time, a rotation speed of the gantry at a certain time, a position of a collimator, an angle of a collimator at a certain time, a shape of the radiation beam at a certain time, a leaf setting parameter of a multi-leaf collimator (MLC), a position and/or an angle of a table (e.g., the table 114) at a certain time, or the like, or a combination thereof.

In some embodiments, the processing device 140 may adjust the one or more parameters in the original treatment plan based on the dose value corresponding to each of the plurality of second voxels and the weight corresponding to each of the plurality of second voxels. In some embodiments, the processing device 140 may adjust and/or optimize the one or more parameters according to an optimization technique. Exemplary optimization techniques may include a direct aperture optimization (DAO) technique or a fluence map optimization (FMO) technique, or the like, or any combination thereof. Specifically, the processing device 140 may determine an optimized fluence map for each beam, and then decompose the optimized fluence maps into deliverable apertures (e.g., the apertures related to position parameters of the MLC leaves and/or the collimator) based on a leaf sequencing algorithm. In an optimized fluence map, a beam may be discretized into a plurality of beamlets, and the intensity of each beamlet may be individually controlled. Accordingly, the processing device 140 may control the intensity of each beamlet based on the dose value corresponding to each of the plurality of second voxels.

In some embodiments, after generating the updated radiation treatment plan, the processing device 140 may compare a first dose distribution in the original treatment plan and a second dose distribution in the updated radiation treatment plan. As used herein, a dose distribution in an image (e.g., a planning image, a treatment image) may refer to the distribution of dose values corresponding to a plurality of voxels in the image (e.g., the plurality of first voxels in the planning image, the plurality of second voxels in the treatment image). The processing device 140 may determine whether the first dose distribution in the original treatment plan and the second dose distribution in the updated radiation treatment plan have similar gradient distribution and/or similar number of hot spots. Hot spots in a dose distribution may refer to a region having locally high doses. In response to a determination that the first dose distribution in the original treatment plan and the second dose distribution in the updated radiation treatment plan have similar gradient distribution and similar number of hot spots, the processing device 140 may determine the updated radiation treatment plan as the radiation treatment plan to be used in the subsequent radiation therapy.

It should be noted that the above description of the process 500 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, operation 501 and operation 502 may be merged into a single operation. As another example, a pre-processing operation may be added before operation 503. The image (e.g. a planning image, a treatment image) may be pre-processed (e.g., filtered, de-noised, classified, or sorted) by the processing device 140. As still another example, a storing operation may be added in process 500. The processing device 140 may store the information and/or data associated with the plurality of first voxels in the planning image and the plurality of the second voxels in the treatment image in a storage medium (e.g., the storage device 150), which is disclosed elsewhere in the present disclosure.

In some embodiments, the plurality of second voxels in the treatment image may be the second voxels of the treatment volume excluding the target of the subject. Accordingly, the method according to the embodiments of the present disclosure may be used for determining dose values corresponding to the plurality of second voxels in the treatment image without contouring most of the VOIs (e.g., the target, the OAR) from the planning image. The method according to the embodiments of the present disclosure may result in increase of acceptance of radiation treatment in daily clinical use by reduction in the need of detail manual inspection/editing of VOIs during online re-planning and by reducing total time to arrive at a new radiation treatment plan.

Figure 6:
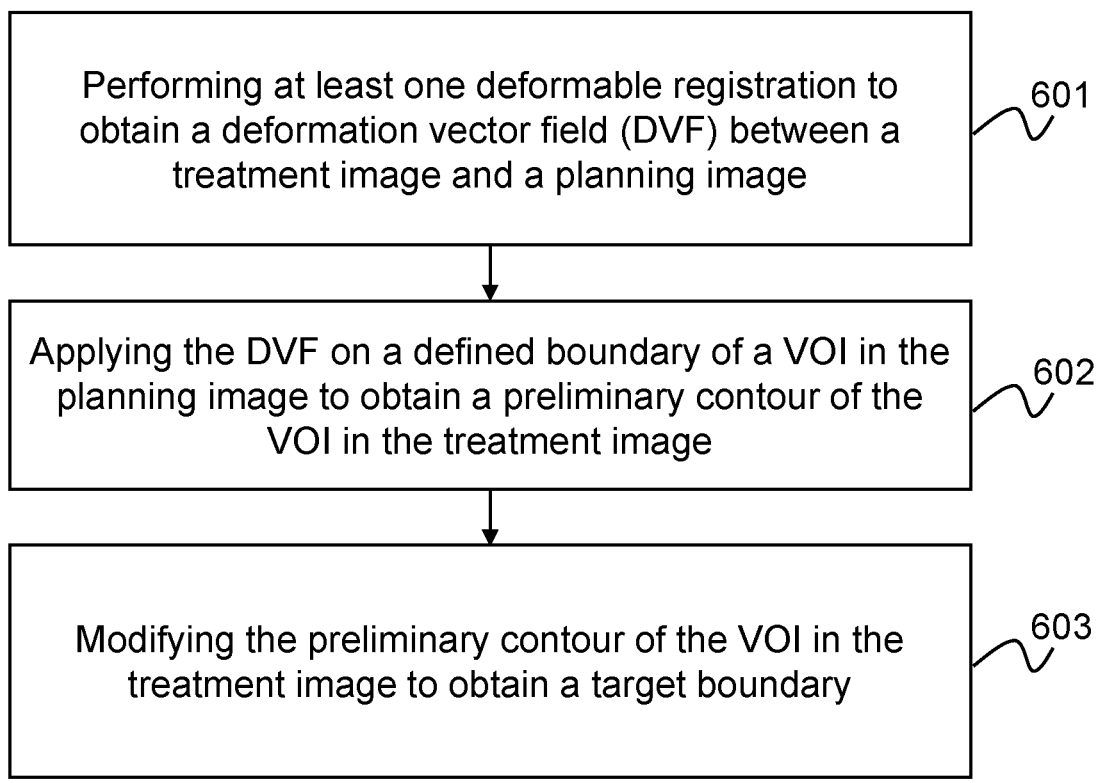
FIG. 6 illustrates a flowchart illustrating an exemplary process for determining a target boundary of a VOI in a treatment image based on a defined boundary of the VOI in a planning image according to some embodiments of the present disclosure.

FIG. 6 illustrates a flowchart illustrating an exemplary process 600 for determining a target boundary of a VOI in a treatment image based on a defined boundary of the VOI in a planning image according to some embodiments of the present disclosure. In some embodiments, at least part of process 600 may be performed by the processing device 140 (implemented in, for example, the computing device 200 shown in FIG. 2). For example, the process 600 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 601, the processing device 140 (e.g., the registration module 404) may perform at least one deformable registration to obtain a deformation vector field (DVF) between a treatment image of a subject (e.g., the treatment image described in operation 502) and a planning image of the subject (e.g., the planning image described in operation 501).

In some embodiments, one or more VOIs (e.g., one or more tumors, one or more OARs) may be presented in both of the treatment image and the planning image. The DVF may represent a mapping relationship between a plurality of third voxels of a VOI in the planning image and a plurality of fourth voxels of the VOI in the treatment image. In some embodiments, the DVF may include a plurality of vectors, with each vector corresponding to a third voxel in the planning image. Each vector in the DVF may have a direction that represents the direction in which a third voxel in the planning image shall move in order to reach a position of a corresponding fourth voxel in the treatment image. Each vector in the DVF may also have a magnitude that represents a distance that the third voxel in the planning image shall travel in the corresponding direction in order to reach the position of the corresponding fourth voxel in the treatment image.

In some embodiments, the processing device 140 may determine the DVF between the planning image and the treatment image according to one or more deformable registration algorithms. The deformable registration algorithms may include a radial basis function (e.g., a thin-plate or surface splines transformation, a multiquadric transformation, or a compactly-supported transformation), a physical continuum model, a large deformation model (e.g., diffeomorphisms), or the like, or any combination thereof.

In 602, the processing device 140 (e.g., the registration module 404) may apply the DVF on a defined boundary of a VOI in the planning image to obtain a preliminary contour of the VOI in the treatment image. For example, the processing device 140 may determine a plurality of voxels in the treatment image by applying the DVF on a plurality of voxels of the defined boundary of the VOI in the planning image. The processing device 140 may further determine the preliminary contour of the VOI in the treatment image by connecting the determined plurality of voxels in the treatment image.

In 603, the processing device 140 (e.g., the registration module 404) may modify the preliminary contour of the VOI in the treatment image to obtain a target boundary. In some embodiments, the processing device 140 may modify the preliminary contour of the VOI in the treatment image according to, for example, a first user instruction to obtain the target boundary of the VOI in the treatment image. The first user instruction may indicate an adjustment of at least a portion of the preliminary contour of the VOI in the treatment image. For example, the operator may add one or more points/voxels into or delete one or points from the preliminary contour of the VOI in the treatment image displayed on the terminal device (e.g., the terminal 130) of the operator.

In some embodiments, the processing device 140 may designate the preliminary contour of the VOI in the treatment image as the target boundary of the VOI in the treatment directly, or in response to a second user instruction including a confirmation message.

It should be noted that the above description of the process 600 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, operation 603 may be omitted.

Figure 7:
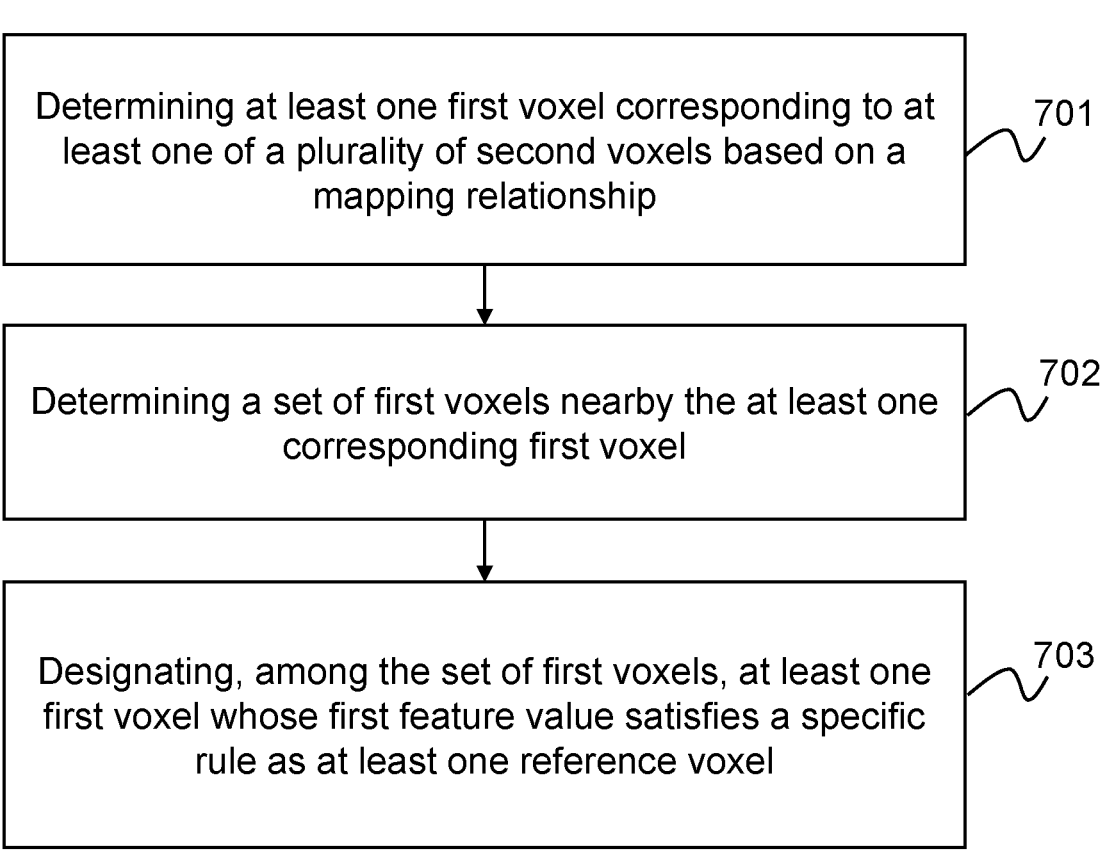
FIG. 7 illustrates a flowchart illustrating an exemplary process for determining one or more reference voxels in a planning image corresponding to a second voxel in a treatment image according to some embodiments of the present disclosure.

FIG. 7 illustrates a flowchart illustrating an exemplary process 700 for determining one or more reference voxels in a planning image corresponding to a second voxel in a treatment image according to some embodiments of the present disclosure. In some embodiments, at least part of process 700 may be performed by the processing device 140 (implemented in, for example, the computing device 200 shown in FIG. 2). For example, the process 700 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting. In some embodiments, operation 504 may be performed according to the process 700.

In 701, the processing device 140 (e.g., the voxel determination module 406) may determine at least one first voxel corresponding to at least one of a plurality of second voxels based on a mapping relationship.

In some embodiments, the mapping relationship may indicate a voxel-to-voxel correspondence between the plurality of second voxels in a treatment image (e.g., the treatment image described in operation 502) and the plurality of first voxels in a planning image (e.g., the planning image described in operation 501). In order to acquire the mapping relationship, the processing device 140 may perform one or more rigid registrations and/or one or more deformable registrations to obtain a deformation vector field (DVF) between the treatment image and the planning image. Then, the processing device 140 may apply the DVF on each second voxel in the treatment image to locate the corresponding first voxel in the planning image.

In 702, the processing device 140 (e.g., the voxel determination module 406) may determine a set of first voxels nearby the at least one corresponding first voxel.

In some embodiments, the processing device 140 may determine the set of first voxels based on the distance between each first voxel and the corresponding first voxel in the planning image. For example, the processing device 140 may determine whether the distance between each of the plurality of first voxels and the corresponding first voxel is smaller than a distance threshold. In response to a determination that the distance between a first voxel and the corresponding first voxel is smaller than the distance threshold, the processing device 140 may determine that the first voxel is in the set of first voxels. The distance threshold may be set manually by an operator, or be determined by one or more components of the radiation therapy system 100 according to default settings. The distance between each first voxel and the corresponding first voxel may be a physical distance or a radiological distance. As used herein, a physical distance between a first voxel and the corresponding first voxel may refer to the length of the shortest path between the first voxel and the corresponding first voxel in the planning image (e.g., the length of the line segment connecting the first voxel and the corresponding first voxel in the planning image). The radiological distance between a first voxel and the corresponding first voxel may be determined by multiplying the electron density along a path between the first voxel and the corresponding first voxel, and the physical distance between the first voxel and the corresponding first voxel. In some embodiments, if the path between the first voxel and the corresponding first voxel crosses a plurality of voxels with different electron densities, the processing device 140 may multiply the electron density of each of the plurality of voxels and a path-length corresponding to the each of the plurality of voxels, respectively. The processing device 140 may further determine the radiological distance between the first voxel and the corresponding first voxel by summing up the plurality of multiplied results.

In 703, the processing device 140 (e.g., the voxel determination module 406) may designate, among the set of first voxels, at least one first voxel whose first feature value satisfies a specific rule as at least one reference voxel.

In some embodiments, the specific rule may be that the first feature value of a first voxel is equal to or close to the second feature value of a specific second voxel (of the at least one of the plurality of second voxels). As used herein, the "close to" may denote that the difference between the first feature value of the first voxel and the second feature value of the specific second voxel is smaller than a feature value threshold. The feature value threshold may be a constant value or a variable value. The variable value may be a percentage of the second feature value of the specific second voxel. Specifically, the variable value may be 0.5%, 1%, 2%, 5%, 10%, etc., of the second value of the specific second voxel.

In some embodiments, the feature value of a voxel (e.g., the first feature value of the reference voxel, the second feature value of the second voxel) may include a Hounsfield unit (HU) value or a gray value corresponding to the voxel as described in connection with operation 501. The HU value and/or the gray value of the reference voxel being equal to or close to the HU value and/or the gray value of the second voxel may indicate that the reference voxel and the second voxel belong to a similar tissue type.

It should be noted that the above description of the process 700 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure.

FIG. 8 illustrates a flowchart illustrating an exemplary process 800 for determining a dose value corresponding to a second voxel according to some embodiments of the present disclosure. In some embodiments, at least part of the process 800 may be performed by the processing device 140 (implemented in, for example, the computing device 200 shown in FIG. 2). For example, the process 800 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting. In some embodiments, operation 505 may be performed according to the process 800.

In 801, for each of at least one reference voxel (e.g., the at least one reference voxel described in connection with operation 504 or operation 703), the processing device 140 (e.g., the dose determination module 408) may determine its distance with respect to a defined boundary of a VOI (e.g., a tumor, a target) in a planning image.

As described elsewhere in the present disclosure, the at least one reference voxel may be selected from a set of the first voxels in the planning image. In some embodiments, for each first voxel in the planning image, the processing device 140 may determine its distance with respect to the defined boundary of the VOI in the planning image, and store the first voxel and its distance with respect to the defined boundary of the VOI in the planning image in a storage device (e.g., the storage device 150) of the radiation therapy system 100, or an external storage device. In some embodiments, the distance of each first voxel with respect to the defined boundary of the VOI in the planning image may be the closest distance from each first voxel to the defined boundary of the VOI in the planning image. In some embodiments, the processing device 140 may determine the closest distance from each first voxel to the defined boundary of the VOI in the planning image based on a signed distance function (SDF). The first voxels and their corresponding distances with respect to the defined boundary of the VOI in the planning image may be recorded in the form of a table, a map, a hash function, or the like. For each of the at least one reference voxel, the processing device 140 may access the storage device and retrieve its distance with respect to the defined boundary of the VOI in the planning image.

In 802, for each of the at least one second voxel, the processing device 140 (e.g., the dose determination module 408) may determine its distance with respect to a target boundary of the VOI in a treatment image. In some embodiments, the target boundary of the VOI in the treatment image may be determined by the process 600.

In some embodiments, the determination of the distance of a second voxel with respect to the target boundary of the VOI in the treatment image may be similar to the determination of the distance of a first voxel with respect to the defined boundary of a VOI in the planning image as described above. The distance of each second voxel with respect to the target boundary of the VOI in the treatment image may be the closest distance from each second voxel to the target boundary of the VOI in the treatment image. In some embodiments, the processing device 140 may determine the closest distance from each second voxel to the target boundary of the VOI in the treatment image based on a signed distance function (SDF).

In some embodiments, for each second voxel in the treatment image, the processing device 140 may store the second voxel and its distance with respect to the target boundary of the VOI in the treatment image in a storage device (e.g., the storage device 150) of the radiation therapy system 100, or an external storage device. For example, the second voxels and their corresponding distances with respect to the target boundary of the VOI in the treatment image may be recorded in the form of a table, a map, a hash function, or the like. For each of the at least one second voxel, the processing device 140 may access the storage device and retrieve its distance with respect to the target boundary of the VOI in the treatment image.

In 803, for each of the at least one reference voxel, the processing device 140 (e.g., the dose determination module 408) may determine a dose per unit distance value based on its initial dose value and its distance with respect to the defined boundary of the VOI in the planning image.

In some embodiments, the processing device 140 may determine the dose per unit distance value of the reference voxel by dividing the initial dose value by the distance with respect to the defined boundary of the VOI in the planning image. Merely for illustration purposes, the dose per unit distance value of the reference voxel may be determined according to Equation (1):

$$A_i = D_i / PSDF_i \quad (1)$$

where $A_i$ refers to the dose per unit distance value of a reference voxel i, $D_i$ refers to the initial dose value corresponding to the reference voxel i, and $PSDF_i$ refers to the distance of the reference voxel i with respect to the defined boundary of the VOI in the planning image.

In 804, the processing device 140 (e.g., the dose determination module 408) may determine a dose value corresponding to the at least one second voxel based on an average of the dose per unit distance values and the distance of the at least one second voxel with respect to the target boundary of the VOI in the treatment image.

In some embodiments, the average of the dose per unit distance values may be an arithmetic mean, a harmonic mean, a geometric mean, or the like. As used herein, the arithmetic mean of n values may be defined as the sum of the n values divided by the total number of the values (i.e., n). The harmonic mean of n values may be defined as the reciprocal of the arithmetic mean of the reciprocals of the n values. The geometric mean of n values may be defined as the nth root of the product of the n values. Merely for illustration purposes, the average of the dose per unit distance values corresponding to the one or more reference voxels may be an arithmetic mean determined according to Equation (2):

$$B = \frac{1}{M} \sum_{i=1}^{M} A_i \quad (2)$$

where B refers to the average of the dose per unit distance values corresponding to the one or more reference voxels, $A_i$ refers to the dose per unit distance value of a reference voxel i, and M refers to the number of the one or more reference voxels corresponding to the at least one second voxel.

Further, the processing device 140 may determine the dose value corresponding to the at least one second voxel based on the average of the dose per unit distance values of the one or more reference voxels corresponding to the at least one second voxel and the distance of the at least one second voxel with respect to the target boundary of the VOI in the treatment image. For example, the processing device 140 may determine the dose value corresponding to a second voxel according to Equation (3):

$$\text{Goal } A_j = B \times TSDF_j \quad (3)$$

where Goal $A_j$ refers to the dose value corresponding to a second voxel j, B refers to the average of the dose per unit distance values corresponding to one or more reference voxels corresponding to the second voxel j, and $TSDF_j$ refers to the distance of the second voxel j with respect to the target boundary of the VOI in the treatment image.

In some embodiments, the dose per unit distance value of each reference voxel may be calculated according to parallel processing. For example, the processing device 140 may determine the dose per unit distance values of the one or more reference voxels via a plurality of threads or a plurality of computing nodes. Specifically, the processing device 140 may determine a first dose per unit distance value of a first reference voxel via a thread X1, a second dose per unit distance value of a second reference voxel via a thread X2, and so on, simultaneously. Additionally, when the determination of a dose per unit distance value of a reference voxel is completed, the corresponding thread may be idle and the idle thread may be assigned a next task, e.g., calculating another dose per unit distance value of another reference voxel.

It should be noted that the above description of the process 600 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure.

Figure 9:
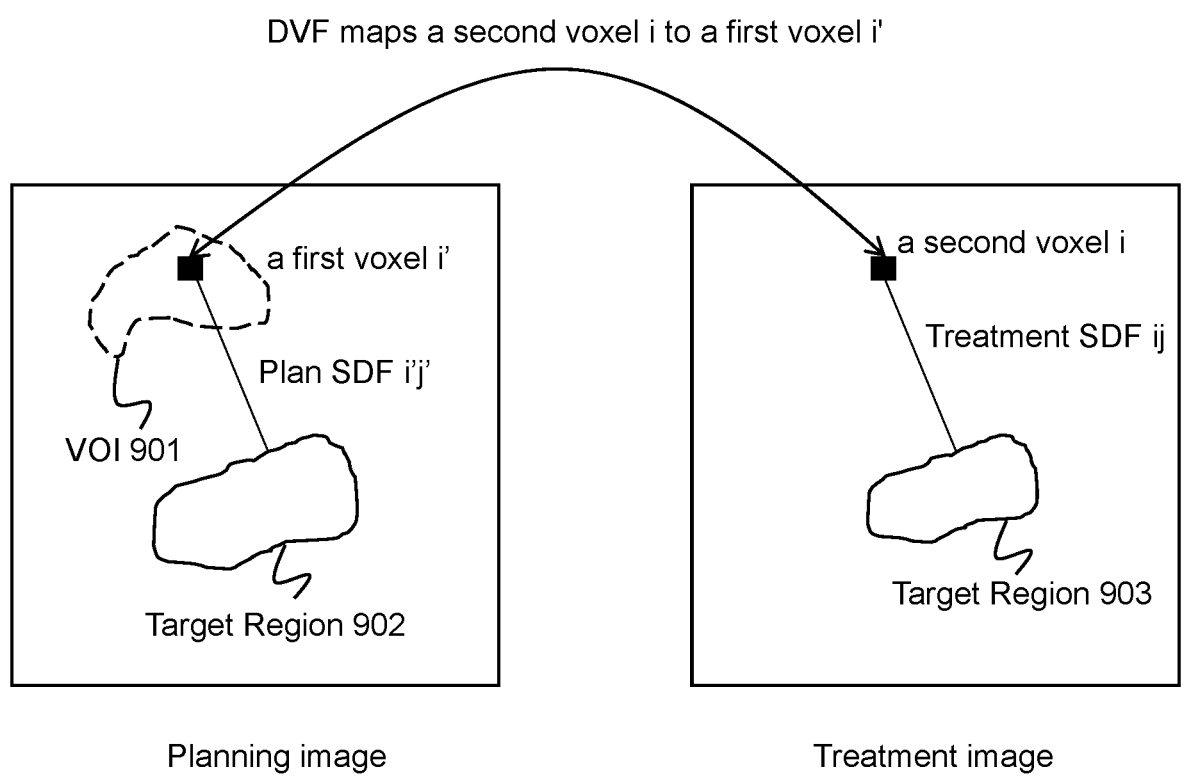
FIG. 9 is a schematic diagram illustrating a DVF connecting voxels of a treatment image and voxels of a planning image according to some embodiments of the present disclosure.

FIG. 9 is a schematic diagram illustrating a DVF connecting voxels of a treatment image and voxels of a planning image according to some embodiments of the present disclosure. As illustrated in FIG. 9, a planning image may include a VOI 901 (e.g., an OAR) and a target region 902. The VOI 901 may include a first voxel i'. The processing device 140 may determine a corresponding second voxel i in a treatment image based on the first voxel i' and a DVF. For example, the processing device 140 may apply the DVF on the first voxel i' in the planning image to locate the corresponding second voxel i in the treatment image. The processing device 140 may also determine a target region 903 in the treatment image corresponding to the target region 902 based on the DVF. For example, the processing device 140 may apply the DVF on a defined boundary of the target region 902 in the planning image to obtain a preliminary contour of the target region 903 in the treatment image. In some embodiments, the processing device 140 may designate the preliminary contour of the target region 903 as the target boundary of the target region 903 in the treatment image. In some embodiments, the processing device 140 may further modify the preliminary contour of the target region 903 in the treatment image according to a user instruction to obtain the target boundary of the target region 903 in the treatment image. The processing device 140 may determine a distance of the first voxel i' in the planning image with respect to the target region 902, e.g., a plan SDF i'j' as illustrated in FIG. 9 (e.g., $PSDF_i$ as described in FIG. 8), and a distance of the second voxel i with respect to the target region 903 in the treatment image, e.g., a treatment SDF ij as illustrated in FIG. 9 (e.g., $TSDF_j$ as described in FIG. 8).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for generating a radiation treatment plan for a treatment volume of a subject, implemented on at least one machine each of which includes at least one processor and at least one storage device, the method comprising:
   retrieving a planning image of the treatment volume, the planning image including a plurality of first voxels, each of the plurality of first voxels corresponding to an initial dose value;
   retrieving a treatment image that represents at least part of the treatment volume, the treatment image including a plurality of second voxels;
   registering the treatment image with the planning image to obtain a mapping relationship between the plurality of second voxels in the treatment image and the plurality of first voxels in the planning image;
   for each of at least one of the plurality of second voxels,
      determining a corresponding first voxel of the second voxel based on the mapping relationship;
      determining a set of first voxels, a distance between each first voxel in the set of first voxels and the corresponding first voxel being smaller than a distance threshold;
      determining, among the set of first voxels, at least one first voxel as at least one reference voxel corresponding to the second voxel, a first feature value of each of the at least one first voxel being equal to or close to a second feature value of the second voxel; and
      determining a dose value of the second voxel based on the at least one initial dose value of the at least one reference voxel; and
   generating a radiation treatment plan by updating an original treatment plan associated with the planning image based at least part on the dose value corresponding to the at least one second voxel.

2. The method of claim 1, wherein the first feature value corresponding to a first voxel includes a gray value of the first voxel or a Hounsfield unit (HU) value corresponding to the first voxel.

3. The method of claim 1, wherein:
   the treatment volume includes a volume of interest (VOI) which is represented in the planning image and in the treatment image, the VOI in the planning image has a defined boundary, wherein:
   the registering the treatment image with the planning image includes:
      performing at least one deformable registration to obtain a deformation vector field (DVF) between the VOI in the treatment image and the VOI in the planning image; and
      determining a target boundary of the VOI in the treatment image at least by applying the DVF on the defined boundary of the VOI in the planning image.

4. The method of claim 3, wherein the determining the target boundary of the VOI in the treatment image further includes:
   applying the DVF on the defined boundary of the VOI in the planning image to obtain a preliminary contour of the VOI in the treatment image; and
   modifying the preliminary contour of the VOI in the treatment image to obtain the target boundary.

5. The method of claim 3, wherein for each of at least one of the plurality of second voxels, the determining the dose value of the second voxel based on the at least one initial dose value of the at least one reference voxel includes:
   for each of the at least one reference voxel, determining its distance with respect to the defined boundary of the VOI in the planning image;
   determining a distance of the second voxel with respect to the target boundary of the VOI in the treatment image; and
   determining the dose value of the second voxel based on the at least one initial dose value of the at least one reference voxel, the at least one distance of the at least one reference voxel with respect to the defined boundary of the VOI in the planning image, and the distance of the second voxel with respect to the target boundary of the VOI in the treatment image.

6. The method of claim 5, wherein the distance of each of the at least one reference voxel with respect to the defined boundary of the VOI in the planning image is the closest distance from each reference voxel to the defined boundary of the VOI in the planning image.

7. The method of claim 5, wherein:
   for each of the plurality of first voxels, its corresponding first feature value and its distance with respect to the defined boundary of the VOI in the planning image is stored in a first data structure; and
   for each of the plurality of second voxels, its corresponding second feature value and its distance with respect to the target boundary of the VOI in the treatment image is stored in a second data structure.

8. The method of claim 5, wherein for each of at least one of the plurality of second voxels, the determining the dose value of the second voxel includes:
   determining, for each of the at least one reference voxel, a dose per unit distance value based on the corresponding initial dose value and its corresponding distance with respect to the defined boundary of the VOI in the planning image; and
   determining the dose value corresponding to second voxel based on an average of the dose per unit distance values corresponding to the at least one reference voxel and the distance of the second voxel with respect to the target boundary of the VOI in the treatment image, wherein the average of the dose per unit distance values is an arithmetic mean, a harmonic mean, or a geometric mean.

9. The method of claim 8, wherein the dose per unit distance value for the at least one reference voxel or the dose value corresponding to the at least one second voxel is calculated according to parallel processing.

10. The method of claim 1, wherein the generating the radiation treatment plan by updating an original treatment plan associated with the planning image based at least part on the dose value corresponding to the at least one second voxel includes:
    adjusting one or more parameters in the original treatment plan associated with the planning image based at least part on the dose value corresponding to the at least one second voxel.

11. The method of claim 1, wherein each of the plurality of second voxels corresponds to a weight, and wherein the generating the radiation treatment plan by updating an original treatment plan associated with the planning image based at least part on the dose value corresponding to the at least one second voxel includes:
    adjusting one or more parameters in the original treatment plan associated with the planning image based on the dose value corresponding to the at least one second voxel and the weight corresponding to the at least one second voxel.

12. The method of claim 1, wherein the treatment volume includes a target to be treated, and the plurality of second voxels in the treatment image are associated with the treatment volume excluding the target.

13. A system comprising:
at least one storage device storing a set of instructions; and
at least one processor in communication with the at least one storage medium, wherein when executing the set of instructions, the at least one processor is configured to cause the system to:
retrieve a planning image of the treatment volume, the planning image including a plurality of first voxels, each of the plurality of first voxels corresponding to an initial dose value;
retrieve a treatment image that represents at least part of the treatment volume, the treatment image including a plurality of second voxels;
register the treatment image with the planning image to obtain a mapping relationship between the plurality of second voxels in the treatment image and the plurality of first voxels in the planning image;
for each of at least one of the plurality of second voxels,
determining a corresponding first voxel of the second voxel based on the mapping relationship;
determining a set of first voxels, a distance between each first voxel in the set of first voxels and the corresponding first voxel being smaller than a distance threshold;
determining, among the set of first voxels, at least one first voxel as at least one reference voxel corresponding to the second voxel, a first feature value of each of the at least one first voxel being equal to or close to a second feature value of the second voxel; and
determine a dose value of the second voxel based on the at least one initial dose value of the at least one reference voxel; and
generate a radiation treatment plan by updating an original treatment plan associated with the planning image based at least part on the dose value corresponding to the at least one second voxel.

14. The system of claim 13, wherein the first feature value corresponding to a first voxel includes a gray value of the first voxel or a Hounsfield unit (HU) value corresponding to the first voxel.

15. The system of claim 13, wherein:
the treatment volume includes a volume of interest (VOI) which is represented in the planning image and in the treatment image, the VOI in the planning image has a defined boundary, and to register the treatment image with the planning image, the at least one processor is configured to cause the system to:
perform at least one deformable registration to obtain a deformation vector field (DVF) between the VOI in the treatment image and the VOI in the planning image; and
determine a target boundary of the VOI in the treatment image at least by applying the DVF on the defined boundary of the VOI in the planning image.

16. The system of claim 15, wherein to determine the target boundary of the VOI in the treatment image, the at least one processor is configured to cause the system to:

apply the DVF on the defined boundary of the VOI in the planning image to obtain a preliminary contour of the VOI in the treatment image; and
modify the preliminary contour of the VOI in the treatment image to obtain the target boundary.

17. The system of claim 15, wherein for each of at least one of the plurality of second voxels, to determine the dose value of the second voxel based on the at least one initial dose value of the at least one reference voxel, the at least one processor is configured to cause the system to:
for each of the at least one reference voxel, determine its distance with respect to the defined boundary of the VOI in the planning image;
determine a distance of the second voxel with respect to the target boundary of the VOI in the treatment image; and
determine the dose value of the second voxel based on the at least one initial dose value of the at least one reference voxel, the at least one distance of the at least one reference voxel with respect to the defined boundary of the VOI in the planning image, and the distance of the second voxel with respect to the target boundary of the VOI in the treatment image.

18. A non-transitory computer readable medium, comprising at least one set of instructions, wherein when executed by at least one processor of a computing device, the at least one set of instructions cause the at least one processor to effectuate a method comprising:
retrieving a planning image of the treatment volume, the planning image including a plurality of first voxels, each of the plurality of first voxels corresponding to an initial dose value;
retrieving a treatment image that represents at least part of the treatment volume, the treatment image including a plurality of second voxels;
registering the treatment image with the planning image to obtain a mapping relationship between the plurality of second voxels in the treatment image and the plurality of first voxels in the planning image;
for each of at least one of the plurality of second voxels,
determining a corresponding first voxel of the second voxel based on the mapping relationship;
determining a set of first voxels, a distance between each first voxel in the set of first voxels and the corresponding first voxel being smaller than a distance threshold;
determining, among the set of first voxels, at least one first voxel as at least one reference voxel corresponding to the second voxel, a first feature value of each of the at least one first voxel being equal to or close to a second feature value of the second voxel; and
determining a dose value of the second voxel based on the at least one initial dose value of the at least one reference voxel; and
generating a radiation treatment plan by updating an original treatment plan associated with the planning image based at least part on the dose value corresponding to the at least one second voxel.

* * * * *